United States Patent [19]
Li

[11] Patent Number: 5,643,266
[45] Date of Patent: Jul. 1, 1997

[54] METHOD AND APPARATUS FOR SECURING LIGAMENTS

[75] Inventor: Lehmann K. Li, Milford, Conn.

[73] Assignee: Li Medical Technologies, Inc., Shelton, Conn.

[21] Appl. No.: 465,559

[22] Filed: Jun. 5, 1995

[51] Int. Cl.$^6$ .................................................. A61B 17/56
[52] U.S. Cl. ................................ 606/72; 606/73; 606/65; 606/96; 623/13; 623/15
[58] Field of Search .................................... 606/72, 73, 75, 606/79, 80, 88, 96; 623/13, 15, 16, 18, 20

[56] References Cited

U.S. PATENT DOCUMENTS

| Re. 34,293 | 6/1993 | Goble et al. . |
|---|---|---|
| Re. 34,762 | 10/1994 | Goble et al. . |
| 1,247,621 | 11/1917 | Bennett . |

(List continued on next page.)

FOREIGN PATENT DOCUMENTS

| 0270704 | 6/1988 | European Pat. Off. . |
|---|---|---|
| 1368021 | 6/1964 | France . |
| 2622430 | 5/1989 | France . |
| 343992 | 3/1931 | United Kingdom . |
| 9204874 | 4/1992 | WIPO . |

OTHER PUBLICATIONS

Acufex Microsurgical, Inc., "Single Incision Fixation . . . EndoButton™ As Easy as Passing the Graft".
Mitek Surgical Products, Inc., "The Mitek Ligament Anchor System".
Y. Ishibashi et al., "The Effect Of The ACL Graft Fixation Level On Knee Stability", Musculoskeletal Research Center, Department of Orthopaedic Surgery, University of Pittsburgh Medical Center, pp. 151–156.
Marc J. Friedman, MD, "Patellar Tendon Versus Hamstring ACL Reconstruction", Southern California Orthopedic Institute, Feb. 25, 1996, pp. 182–188.
Linvatec, "The BioScrew Fixation System", 1995.
John Cherf, MD, MPH et al., "Graft Fixation For Anterior Cruciate Ligament Reconstruction" Orthopedic Special Edition, Jun. 1996, pp. 48–51.
Instrument Makar, Inc. "PerFixation™ ACL System", Jun. 1994, pp. 1–12.
Akira Maeda, MD, et al., "Anterior Cruciate Ligament Reconstruction with Multistranded Autogenous Semitendinosus Tendon", The American Journal of Sports Medicine, vol. 24, No. 4, pp. 504–509.
Mark A. Davis, MD, et al., "Sports Medicine Today".

*Primary Examiner*—Michael Buiz
*Assistant Examiner*—Mark S. Leonardo
*Attorney, Agent, or Firm*—Ostrolenk, Faber, Gerb & Soffen, LLP

[57] ABSTRACT

Apparatus for reattaching a ligament or implanting a ligament replacement in bone comprising a first ligament attaching element for coupling to a first end of the ligament or ligament replacement, a second ligament attaching element for coupling to a second end of the ligament or ligament replacement, a first engaging element slidably disposed on the first ligament attaching element and having at least one longitudinally extending finger, a second engaging element slidably disposed on the second ligament attaching element and having at least one longitudinal extending finger. The finger of each engaging element is directed toward the other. The first attaching element and first engaging element are adapted to be inserted in a first bore in a first bone member. The second attaching element and second engaging element are adapted to be inserted in a second bore in a second bone member aligned with the first bore, with the ligament or ligament replacement disposed between the attaching elements and in general alignment with the bores. The first and second attaching elements each having cam surfaces thereon for engaging the at least one finger of the respective engaging element. The finger of each engaging element is adapted to be moved into engagement with the cam surface thereby to force the finger to move outwardly into engagement with the wall of the bore in the respective bone member, thereby securing the engaging element into the respective bone member with the ligament or ligament replacement attached between the first and second attaching elements.

21 Claims, 7 Drawing Sheets

U.S. PATENT DOCUMENTS

| | | |
|---|---|---|
| 2,100,570 | 11/1937 | Saleh . |
| 2,143,086 | 1/1939 | Pleister . |
| 2,213,715 | 9/1940 | Monahan . |
| 2,453,056 | 11/1948 | Zack . |
| 2,562,419 | 7/1951 | Ferris . |
| 3,048,177 | 8/1962 | Takaro . |
| 3,143,915 | 8/1964 | Tendler . |
| 3,155,095 | 11/1964 | Brown . |
| 3,227,031 | 1/1966 | Williams . |
| 3,254,650 | 6/1966 | Collito . |
| 3,316,796 | 5/1967 | Young . |
| 4,011,602 | 3/1977 | Rybicki et al. . |
| 4,233,981 | 11/1980 | Schomacher . |
| 4,293,259 | 10/1981 | Liebig . |
| 4,379,451 | 4/1983 | Getscher . |
| 4,447,915 | 5/1984 | Weber . |
| 4,454,612 | 6/1984 | McDaniel et al. . |
| 4,501,266 | 2/1985 | McDaniel . |
| 4,525,114 | 6/1985 | Hirst . |
| 4,632,100 | 12/1986 | Somers et al. . |
| 4,636,121 | 1/1987 | Miller . |
| 4,708,132 | 11/1987 | Silvestrini . |
| 4,738,255 | 4/1988 | Goble et al. . |
| 4,741,330 | 5/1988 | Hayhurst . |
| 4,744,793 | 5/1988 | Parr et al. . |
| 4,747,407 | 5/1988 | Liu et al. . |
| 4,759,765 | 7/1988 | Van Kampen . |
| 4,772,286 | 9/1988 | Goble et al. . |
| 4,776,330 | 10/1988 | Chapman et al. . |
| 4,828,562 | 5/1989 | Kenna ................................. 606/72 |
| 4,870,957 | 10/1989 | Goble et al. . |
| 4,875,474 | 10/1989 | Border . |
| 4,892,547 | 1/1990 | Brown . |
| 4,898,156 | 2/1990 | Gatturna . |
| 4,899,743 | 2/1990 | Nicholson et al. . |
| 4,901,711 | 2/1990 | Goble et al. . |
| 4,911,153 | 3/1990 | Border . |
| 4,927,421 | 5/1990 | Goble et al. . |
| 4,946,468 | 8/1990 | Li . |
| 4,959,071 | 9/1990 | Brown et al. . |
| 4,960,420 | 10/1990 | Goble et al. . |
| 4,968,315 | 11/1990 | Gatturna . |
| 4,985,032 | 1/1991 | Goble . |
| 4,986,263 | 1/1991 | Dickerson et al. . |
| 4,997,433 | 3/1991 | Goble et al. . |
| 5,002,550 | 3/1991 | Li . |
| 5,002,574 | 3/1991 | May et al. . |
| 5,011,473 | 4/1991 | Gatturna . |
| 5,013,316 | 5/1991 | Goble et al. . |
| 5,019,105 | 5/1991 | Wiley . |
| 5,037,422 | 8/1991 | Hayhurst et al. . |
| 5,037,426 | 8/1991 | Goble et al. . |
| 5,046,513 | 9/1991 | Gatturna . |
| 5,078,730 | 1/1992 | Li . |
| 5,084,058 | 1/1992 | Li . |
| 5,087,263 | 2/1992 | Li . |
| 5,092,891 | 3/1992 | Kummer et al. . |
| 5,094,563 | 3/1992 | Carletti . |
| 5,129,902 | 7/1992 | Goble et al. . |
| 5,133,723 | 7/1992 | Li et al. . |
| 5,141,520 | 8/1992 | Goble et al. . |
| 5,147,166 | 9/1992 | Harker . |
| 5,147,362 | 9/1992 | Goble . |
| 5,152,764 | 10/1992 | Goble . |
| 5,161,916 | 11/1992 | White et al. . |
| 5,163,946 | 11/1992 | Li . |
| 5,174,087 | 12/1992 | Bruno . |
| 5,176,682 | 1/1993 | Chow . |
| 5,192,303 | 3/1993 | Gatturna et al. . |
| 5,203,787 | 4/1993 | Noblitt et al. . |
| 5,207,679 | 5/1993 | Li . |
| 5,217,486 | 6/1993 | Rice et al. . |
| 5,250,058 | 10/1993 | Miller et al. . |
| 5,263,802 | 11/1993 | Fichot et al. . |
| 5,263,991 | 11/1993 | Wiley et al. . |
| 5,266,075 | 11/1993 | Clark et al. . |
| 5,268,001 | 12/1993 | Nicholson et al. . |
| 5,300,077 | 4/1994 | Howell . |
| 5,306,290 | 4/1994 | Martins et al. . |
| 5,312,416 | 5/1994 | Spaeth et al. . |
| 5,312,422 | 5/1994 | Trott . |
| 5,312,438 | 5/1994 | Johnson . |
| 5,313,962 | 5/1994 | Obenchain . |
| 5,314,427 | 5/1994 | Goble et al. . |
| 5,314,429 | 5/1994 | Goble . |
| 5,314,433 | 5/1994 | Li . |
| 5,318,577 | 6/1994 | Li . |
| 5,324,308 | 6/1994 | Pierce . |
| 5,330,534 | 7/1994 | Herrington et al. . |
| 5,342,366 | 8/1994 | Whiteside et al. . |
| 5,350,380 | 9/1994 | Goble et al. . |
| 5,354,298 | 10/1994 | Lee et al. . |
| 5,354,300 | 10/1994 | Goble et al. . |
| 5,356,413 | 10/1994 | Martins et al. . |
| 5,358,511 | 10/1994 | Gatturna et al. . |
| 5,372,599 | 12/1994 | Martins . |
| 5,372,604 | 12/1994 | Trott . |
| 5,376,120 | 12/1994 | Sarver et al. . |
| 5,393,302 | 2/1995 | Clark et al. . |
| 5,417,691 | 5/1995 | Hayhurst . |
| 5,443,482 | 8/1995 | Stone et al. . |
| 5,464,425 | 11/1995 | Skiba . |
| 5,464,427 | 11/1995 | Curtis et al. . |
| 5,486,197 | 1/1996 | Le et al. . |
| 5,500,001 | 3/1996 | Trott . |
| 5,531,792 | 7/1996 | Huene ................................. 623/16 |
| 5,534,004 | 7/1996 | Santangelo . |
| 5,545,180 | 8/1996 | Le et al. . |
| 5,562,668 | 10/1996 | Johnson . |
| 5,562,669 | 10/1996 | McGuire . |

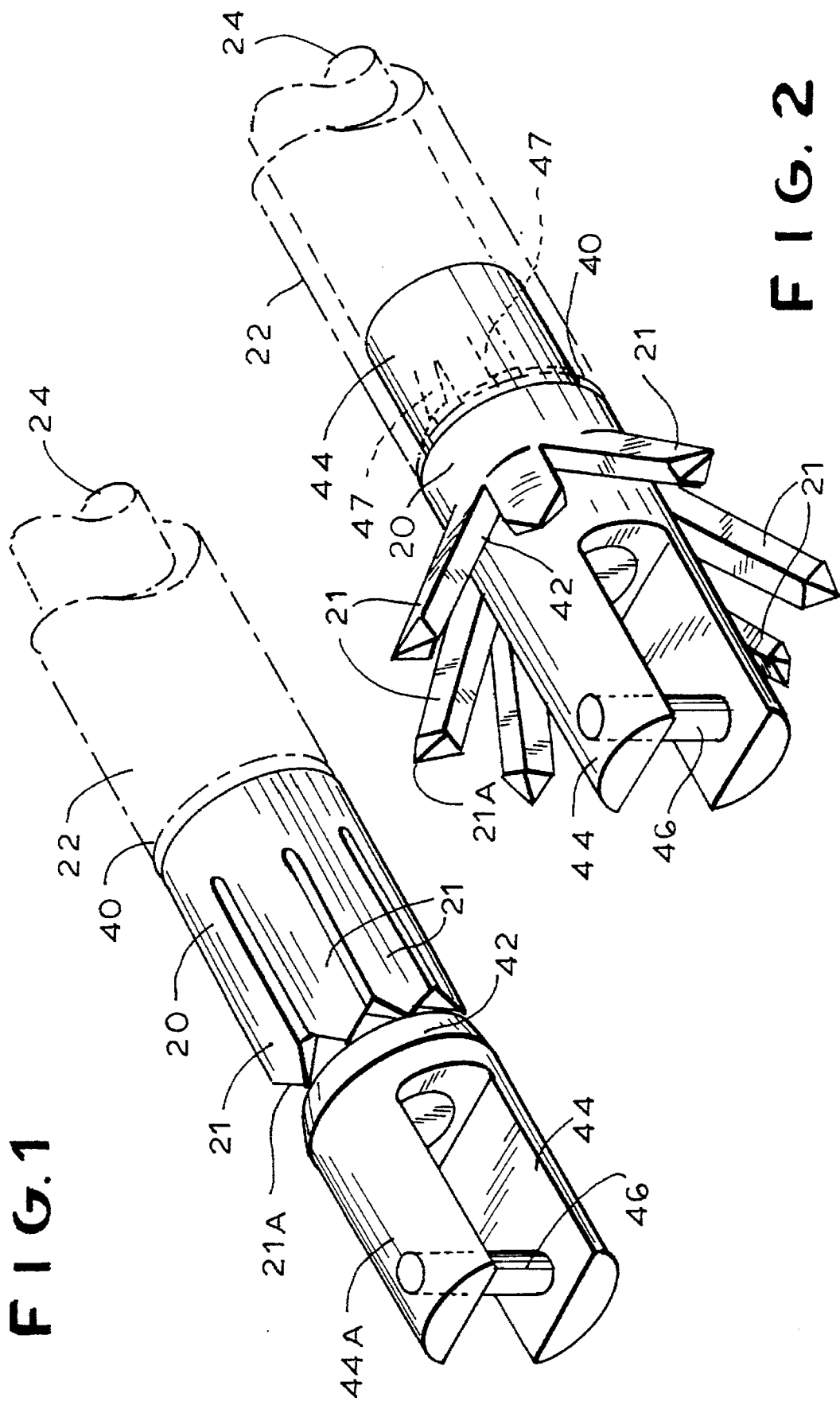

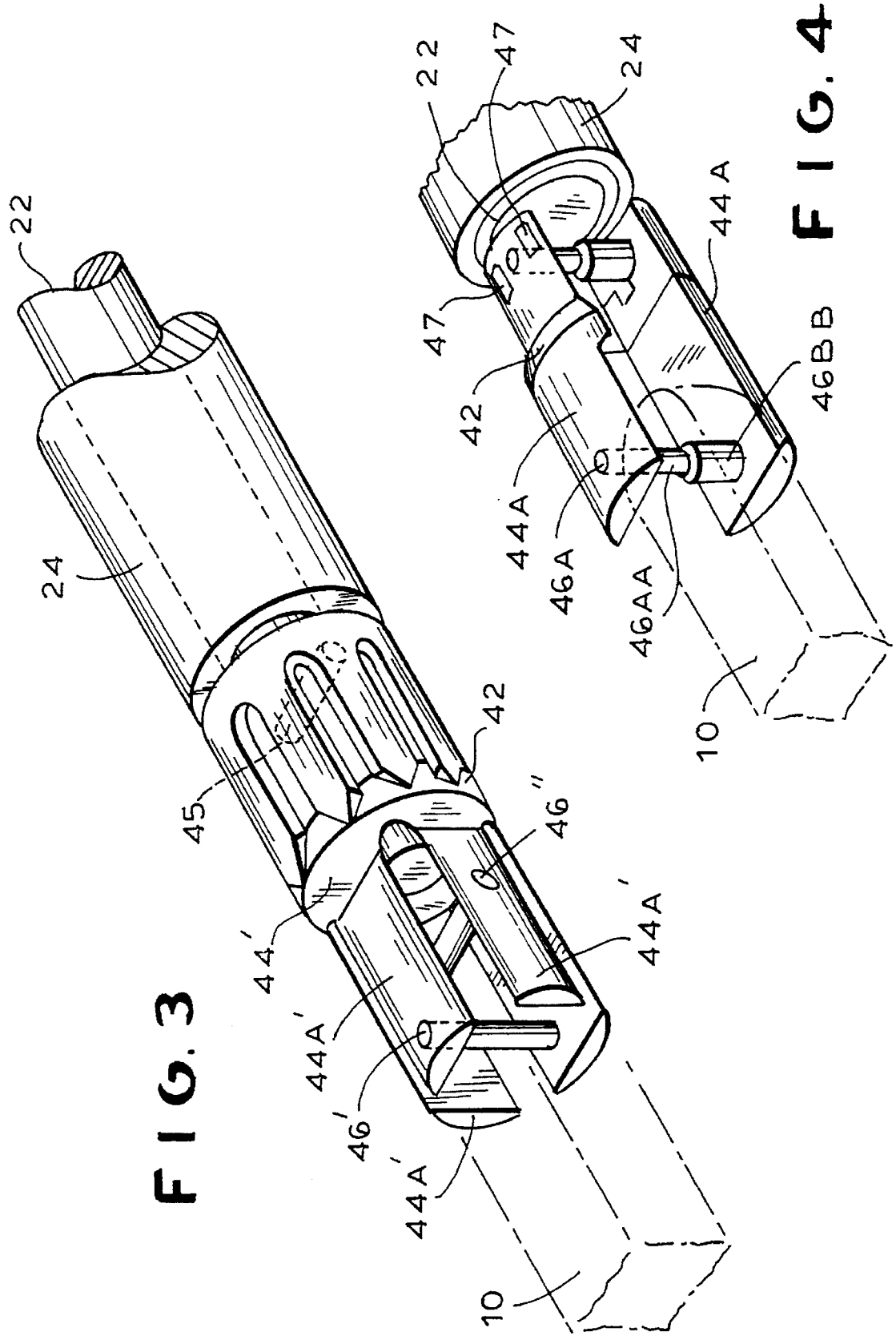

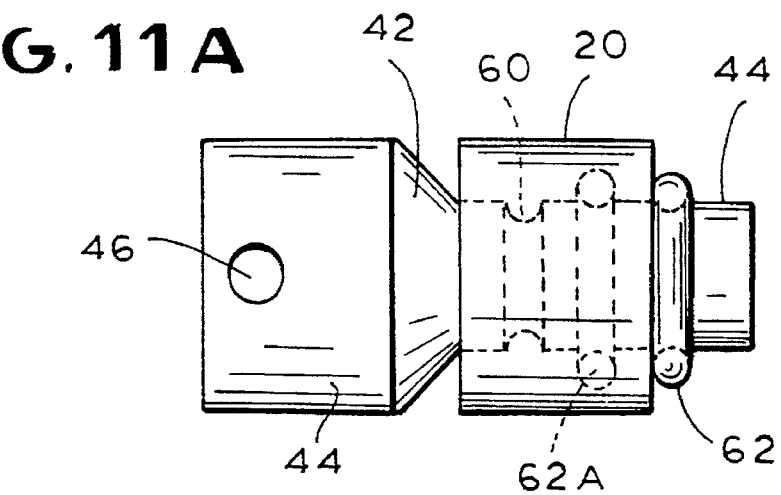
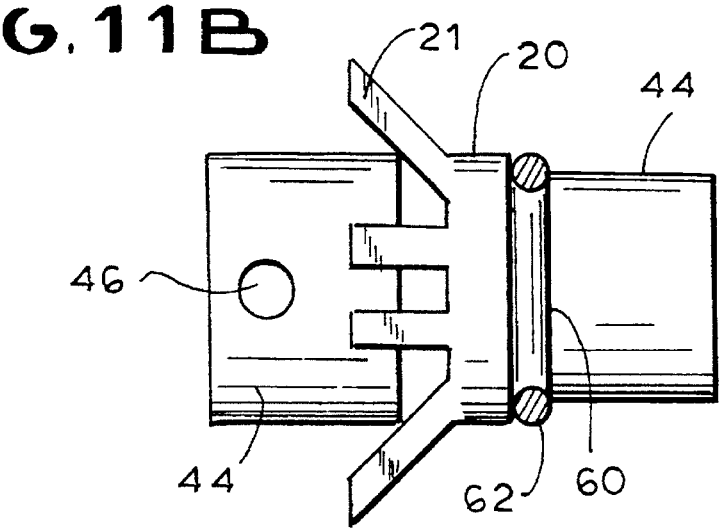
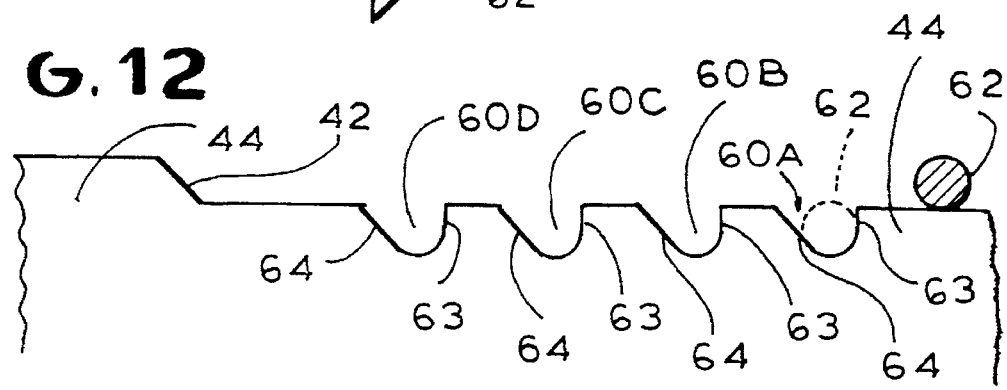

5,643,266

METHOD AND APPARATUS FOR SECURING LIGAMENTS

BACKGROUND OF THE INVENTION

The present invention relates to methods and apparatus for repairing ligaments, and in particular, to a method and apparatus for replacing torn ligaments. Even more particularly, the present invention relates to a method and apparatus for reattaching ligaments or replacing ligaments with man-made substitutes. An example of a ligament of the human body which can be reattached or replaced with a man-made substitute by the method and apparatus of the present invention is the anterior cruciate ligament of the human knee.

It is frequently necessary to repair, and in extreme circumstances, to completely replace torn ligaments, for example ligaments of the human body. An example of a frequently torn ligament is the anterior cruciate ligament located in the human knee.

The present invention provides a method and apparatus for reattaching or replacing ligaments such as the anterior cruciate ligament. It is not limited to such ligament but the application of the present invention to the replacement of that ligament is particularly effective for explanatory purposes.

U.S. Pat. No. RE 34,293 to Goble et al. describes a ligament attachment method and apparatus and in particular, describes such a method and apparatus for the replacement of the cruciate ligaments.

The device of the Goble reference utilizes a prosthetic ligament which includes at one end a flattened cone and at the other end an expandable cone which is expanded by an expansion anchor.

Since the forces tending to rupture the ligament would tend to pull the cones through the bores in the two bones to which the prosthetic ligament is attached, it is believed that the securement method shown in the Goble et al. reference is not sufficiently strong.

SUMMARY OF THE INVENTION

It is, accordingly, an object of the present invention to provide a ligament attachment method and apparatus.

It is yet still a further object of the present invention to provide an apparatus and method for reattaching or replacing torn ligaments.

It is yet still another object of the present invention to provide a ligament or replacement ligament attachment method and apparatus which is extremely secure and prevents pulling out of the ligament from the attachment points.

It is yet still a further object of the present invention to provide a ligament attachment method and apparatus which is convenient for surgeons to use and provides optimum strength.

It is yet still an additional object of the present invention to provide a ligament attachment method and apparatus which uses anchors of the type disclosed in applicant's copending application Ser. No. 08/294,067 filed Aug. 22, 1994.

The above and other objects of the present invention are achieved by an apparatus for reattaching a ligament or implanting a ligament replacement in bone comprising a first ligament attaching element for coupling to a first end of the ligament or ligament replacement, a second ligament attaching element for coupling to a second end of the ligament or ligament replacement, a first engaging element slidably disposed on the first ligament attaching element and having at least one longitudinally extending finger, a second engaging element slidably disposed on the second ligament attaching element and having at least one longitudinally extending finger, the finger of each engaging element being directed toward each other, the first attaching element and first engaging element being adapted to be inserted in a first bore in a first bone member, the second attaching element and second engaging element being adapted to be inserted in a second bore in a second bone member aligned with the first bore, with the ligament or ligament replacement disposed between the attaching elements and in general alignment with the bores, the first and second attaching elements each having cam surfaces thereon for engaging the at least one finger of the respective engaging element, the finger of each engaging element being adapted to be moved into engagement with the cam surface thereby to force the finger to move outwardly into engagement with the wall of the bore in the respective bone member, thereby securing the engaging element into the respective bone member with the ligament or ligament replacement attached between the first and second attaching elements.

The objects of the invention are also achieved by a method for reattaching a ligament or implanting a ligament replacement in bone comprising: coupling at least a first end of the ligament or ligament replacement to a first ligament attaching element; coupling a second end of the ligament or ligament replacement to a second ligament attaching element; providing a first engaging element slidably disposed on the first ligament attaching element and having at least one longitudinally extending finger; providing a second engaging element slidably disposed on the second ligament attaching element and having at least one longitudinally extending finger; making an aligned bore hole in two bone members to be connected by the ligament or ligament replacement; inserting the ligament or ligament replacement with the first attaching element and first engaging element and second attaching element and second engaging element into the aligned bore hole in the first and second bone members such that the first attaching element and first engaging element are positioned in the first bone member and the second attaching element and second engaging element are positioned in the second bone member, with the ligament or ligament replacement disposed between the attaching elements and in general alignment with the aligned bore hole, the finger of each engaging element being directed toward each other, and moving the finger of each engaging element into engagement with a cam surface of the respective attaching element thereby to force the finger to move outwardly into engagement with the wall of the bore in the respective bone member, thereby securing the engaging element into the respective bone member with the ligament or ligament replacement attached between the first and second attaching elements.

The above and other objects of the invention are also achieved by a apparatus for reattaching a ligament or implanting a ligament replacement in bone comprising a first ligament attaching element for coupling to a first end of the ligament or ligament replacement; a first engaging element slidably disposed on the first ligament attaching element and having at least one longitudinally extending finger; the first attaching element and first engaging element being adapted to be inserted in a first bore in a first bone member, with the ligament or ligament replacement disposed between the attaching element and a second bone member; the first attaching element having a cam surface thereon for engaging the at least one finger of the engaging element; the finger of the engaging element being adapted to be moved into engagement with the cam surface thereby to force the finger to move outwardly into engagement with the wall of the bore in the first bone member, thereby securing the engaging element into the first bone member with the ligament or ligament replacement attached to the first attaching element.

In accordance with this embodiment, one end of a ligament or ligament replacement can be secured by the invention, and the other end, as necessary, can be secured by the invention or any other device or method.

The above and other objects are also achieved by a method for reattaching a ligament or implanting a ligament replacement in bone comprising coupling at least a first end of the ligament or ligament replacement to a first ligament attaching element; providing a first engaging element slidably disposed on the first ligament attaching element and having at least one longitudinally extending finger; making a bore hole in a first bone member to be connected by the ligament or ligament replacement; inserting the ligament or ligament replacement with the first attaching element and first engaging element into the bore in the first bone member such that the first attaching element and first engaging element are positioned in the first bone member with the ligament or ligament replacement disposed between the attaching element and a second bone member; moving the finger of the engaging element into engagement with a cam surface of the attaching element thereby to force the finger to move outwardly into engagement with the wall of the bore in the first bone member, thereby securing the engaging element into the first bone member with the ligament or ligament replacement attached to the first attaching element.

Other objects, features and advantages of the present invention will be apparent from the detailed description which follows.

BRIEF DESCRIPTION OF THE DRAWINGS

The invention will now be described in the following detailed description with reference to the drawings in which:

FIG. 1 shows an embodiment of one end of a ligament attachment coupling according to the present invention prior to its activation to secure it into a bore in bone;

FIG. 2 shows the ligament securement device of FIG. 1 in its engagement position whereby it engages into the bore in which it is inserted to secure the ligament thereto;

FIG. 3 shows a second embodiment of the ligament securement device according to the present invention;

FIG. 4 shows another embodiment of the ligament securement device according to the present invention;

FIGS. 11A and 11B show an alternative means of holding the engaging elements into engagement with a bore; and FIG. 12 shows, in a partial view, the structure of FIGS. 11A and 11B modified so as to allow varying degrees of engagement of the engaging element into the bore.

DETAILED DESCRIPTION OF THE INVENTION

Figure 9:
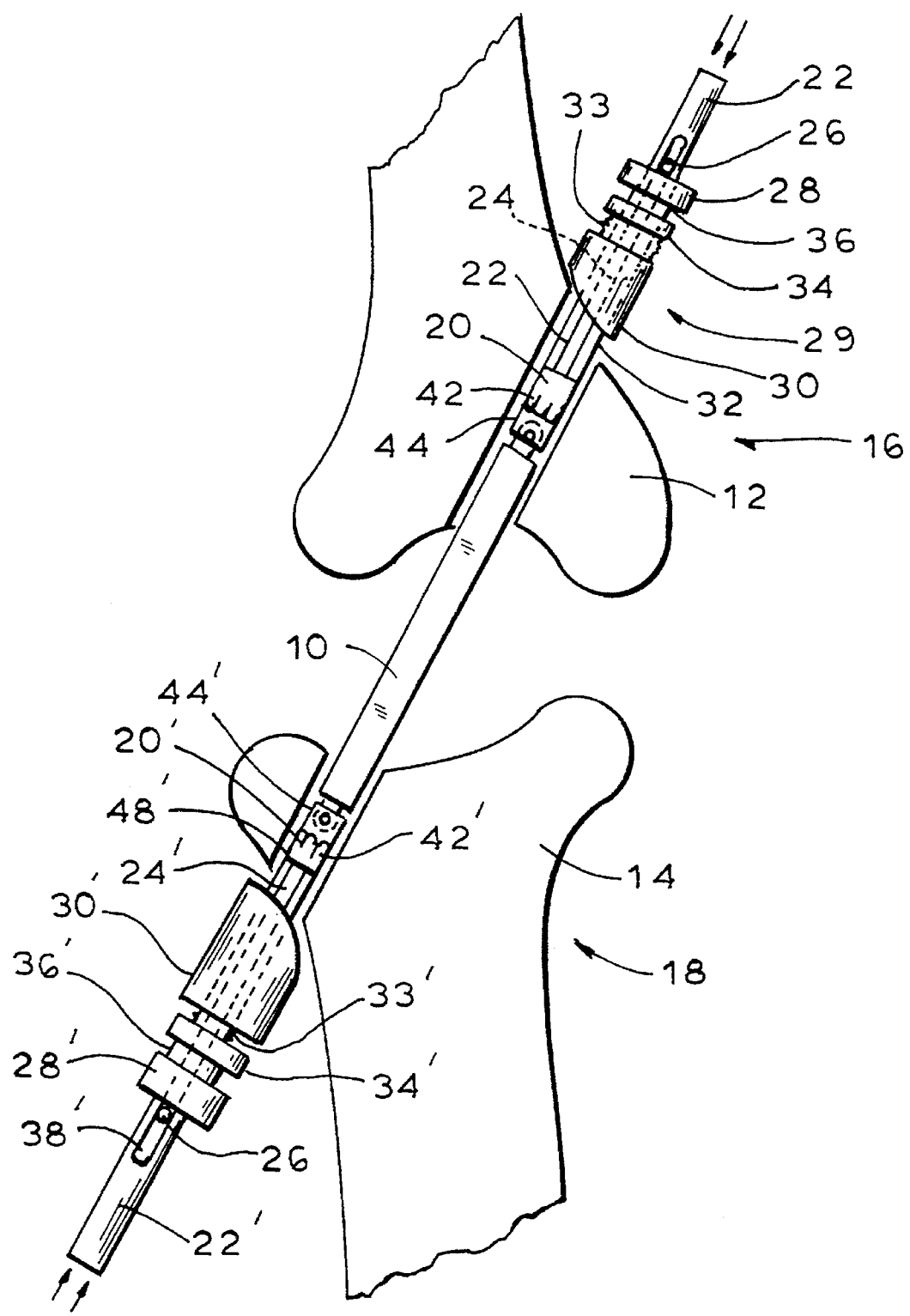
FIG. 9 shows schematically the ligament attaching device according to the present invention in position between two bores, in particular, showing the device being used to replace the anterior cruciate ligaments.
Figure 10:
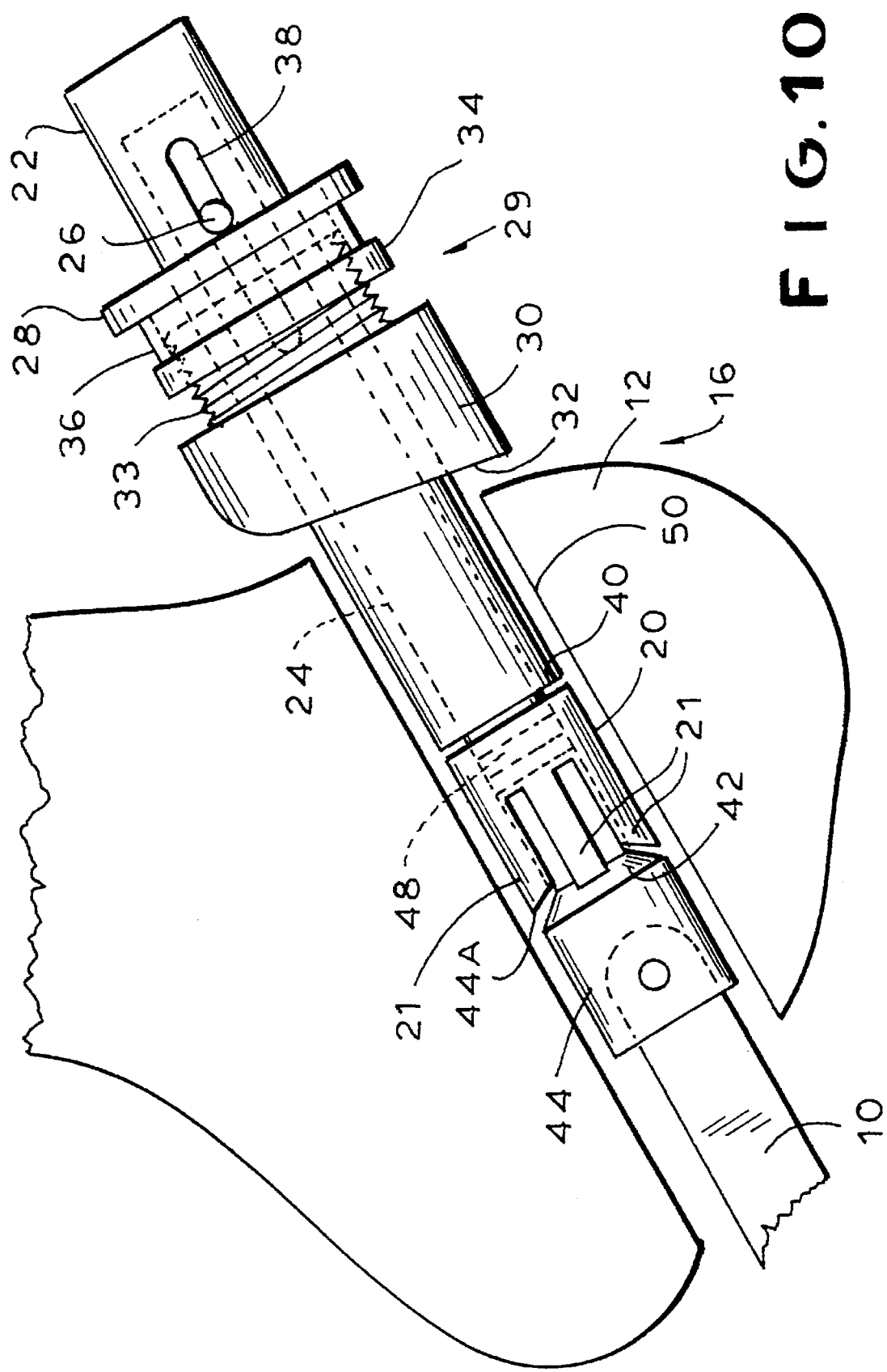
FIG. 10 shows details of a portion of FIG. 9.

With reference now to the drawings, FIG. 9 shows the device according to the present invention in place between two bones for attaching a replacement ligament 10. The device is shown, as an example, installed between the femur 12 and tibia 14 thus comprising a device for reattaching the anterior cruciate ligaments or for replacing same with a replacement ligament 10. The device includes a femoral attachment generally designated 16 and a tibial attachment generally designated 18. The two attachments 16 and 18 are generally similar. FIG. 10 shows details of the attachment 16.

Attachment 16 includes an anchor or fastening device 20, to be described in greater detail below but which is based upon the device described in applicant's above-identified copending patent application. The attachment 16 further includes a cylindrical device 22 through the center of which is disposed a concentric shaft 24 which is removably coupled to the fastener or engaging element 20. The concentric shaft 24 includes a pin 26 disposed therethrough. A collar 28 rides on the cylinder 22 and is held in an abutting relationship with the pin 26. The pin 26 extends through a longitudinally disposed slot in the cylinder 22. Adjacent the collar 28, a pressure applying member 30 is provided which has a shaped 32 adapted to the contour of the bone in which the fastener 20 is being inserted, in the illustrated embodiment, the femur. The contoured pressure applying member 30 has a hollow cylinder 33 attached thereto which has a screw thread on which a nut 34 is threadedly engaged. Between the nut 34 and the collar 28, a spacer 36 is provided that is slidable over the screw threads of cylinder 33.

Pin 26 fixed in shaft 24 slides in a groove 38 in the cylinder 22.

Cylinder 22 has an end 40 which is in engagement with the top of the fastener element 20. Fastener element 20, as disclosed in applicant's above-identified copending patent application, includes a plurality of circumferentially spaced fingers 21 which are adapted to engage a cam surface 42 of a ligament attaching element 44. The fingers 21 have slanted surfaces 21A which are adapted to engage with the slanted surface 42 of the ligament fastening element 44.

At the tibial end 14 of the device, a similar structure is provided. The corresponding elements, because they have the same function, have been identified with the same numbers but with a prime designation.

Figure 7A:
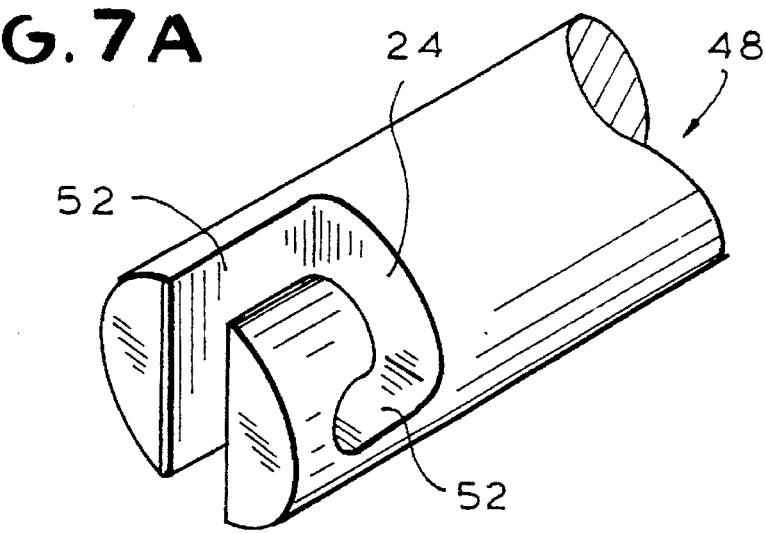
FIG. 7A and 7B show couplings for attaching the securement device of the present invention to an insertion shaft having a removable coupling for inserting the securement device according to the present invention.
Figure 7B:
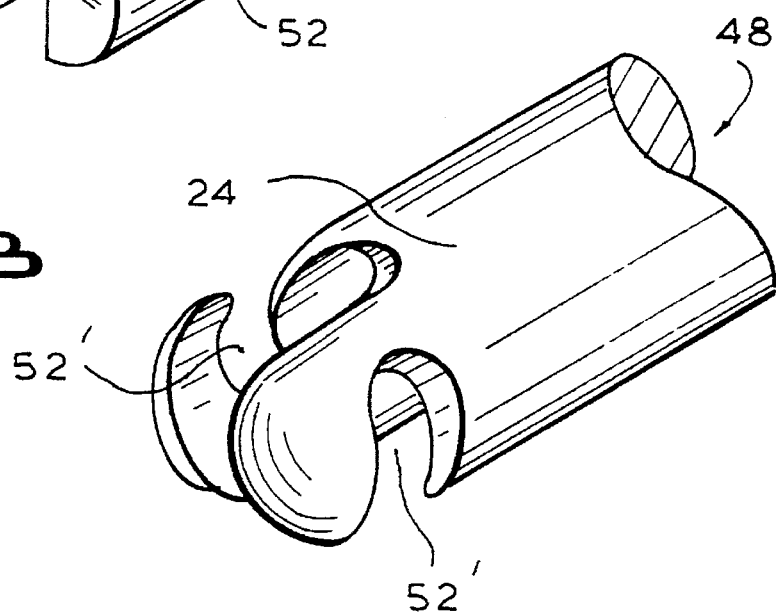
Figure 7C:
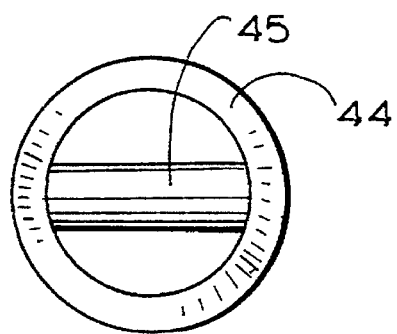
FIG. 7C shows a view along lines 7—7 of FIG. 6.

FIGS. 1 and 2 show the operation of the engaging or fastener element 20 of the ligament attaching device according to the present invention. As discussed above, the engaging element 20 has a plurality of fingers 21. These fingers are flexible and adapted to be forced into engagement with the bore 50 (see FIG. 10) bored into the bone i.e., in the case of the anterior cruciate ligament replacement, an aligned bore in the femur and tibia. The fingers 21 may be provided with sharply pointed or slanted ends 21A which facilitate the penetration of the fingers 20 into the wall of the bore in the bone. The cylinder 22 is disposed in abutting relationship with the fastener element 20 at the location 40. The shaft 24 disposed concentrically in the interior of the cylinder 22 is coupled to the ligament attaching element 44. Ligament attaching element 44 has the cam surface 42 at an end thereof adjacent the fingers 21 of the fastener element 20. Ligament attaching element 44 may include a pin 46 about which the replacement ligament is fastened through a suitable aperture therein or by tying off. The shaft 24 is coupled to the ligament attaching element 44 by a releasable coupling, for example a bayonet coupling, as shown schematically in FIG. 10 at 48. For example, FIGS. 7A and 7B show suitable bayonet type releasable couplings 48 which may be provided to couple the shaft 24 to the element 44. FIG. 7C shows a rear view of the element 44 showing a pin 45 disposed therethrough which is adapted to be received in the slots 52 of the embodiment of FIG. 7A or the slots 52' of the embodiment of FIG. 7B. As known to those of skill in the art, in order to lock the shaft 24 to the element 44, the pin 45 is placed through the slot and then the shaft is turned, thereby locking the shaft in the L-shaped slots 52, 52'.

The device of the present invention is operated as follows. First, a suitable aligned bore 50 is drilled through the respective bones, in the illustrated embodiments the femur and tibia for the replacement of the anterior cruciate ligament. The drilling can be formed by any methods known to those of skill in the art.

Next, the ligament replacement 10 is attached to the ligament attaching elements 44 and 44' by any suitable means, for example by making a hole through the ligament, by tying off, etc. These methods are known to those of skill in the art. A suitable method is to tie off the ligament around the post 46 of the element 44. The ligament with the attaching elements 44, 44' and respective fastener elements 20, 20' are thereafter inserted through the aligned bore so that the elements 20, 20' are disposed in the respective portions of the bore 50 in the respective bones, in this case the femur and tibia. This can be done using the cylinder 22' and shaft 24' at one bone end, e.g. the tibia end. The insertion can also be done at the femoral end. As discussed above, reference numerals with prime designations refer to the tibia end. The assembly comprising the cylinder 22 and shaft 24 together with the tensioning member generally designated 29 is then inserted into the bore 50 at the other bone end (e.g. the femoral end) and the releasable coupling 48 is locked to the pin 45 of the element 44.

In one manner of use, the ligament 10 with both attaching elements 44, 44' (and thus fastener elements 20, 20') at both ends is attached to only one of the insertion-tensioning devices 29, 29' via the releasable coupling 48, 48'. The end of the ligament 10 without the device 29, 29' is then inserted through the bore 50 by grasping the attached device 29 or 29'. Once inserted fully into the bore 50 so that the engaging elements 20, 20' are in appropriate position in the bone elements, the other attachment 29 or 29' is inserted into the bone and coupled via the releasable coupling 48, 48' to the attaching element 44, 44'. Alternatively, the attaching element 44, 44' to which the insertion-tensioning device 29, 29' is not attached can be pushed out of the bore 50, the device 29, 29' coupled thereto via the releasable coupling and the entire assembly pulled or pushed back into the bore in appropriate position. Tension is then applied to the ligament replacement 10 as follows:

The member 30 is adjusted on its screw thread 33 by turning the nut 34 against the free spacer 36, which in turn abuts against the collar 28 which is fixed in position by the pin 26 through the shaft 24. By turning the nut 34 in the appropriate direction, the contoured element 30 can be brought into contact with the patient's body near the bore 50 in the bone, thereby applying a tension on the shaft 24 and thus to the ligament 10. A similar procedure is performed at the tibial end 18, so as to bring the contoured element 30' into engagement with the patient's body, thereby tensioning the replacement ligament 10. Although an adjusting nut 28' is provided at the tibial end, it may not be necessary to provide an adjustment at both femoral and tibial ends, since one adjustment at one end can suffice. However, to provide maximum flexibility, such an adjusting mechanism to provide tension on the ligament 10 can be provided at both ends of the device.

The adjusting nuts 34, 34' are thus adjusted to provide the proper amount of tension on the ligament 10. With the proper amount of tension applied, a force is now applied (separately, at different times or simultaneously) to the ends of the cylinders 22, 22', which causes the cylinders 22, 22' to move toward the respective engaging elements 20, 20'. This causes the fingers 21 of the engaging elements 20, 20' to come into contact with the cam surface 42, 42' of the ligament attaching elements 44. This causes the fingers 21, 21" to flex, riding up on the cam surface 42, 42" as shown in FIG. 2. The fingers 21 engage with the inner wall of the bore 50, penetrating or biting into the bore thereby to secure the element 20, 20' in the bore 50 in the bone.

Now that the elements 20, 20' have been secured with the proper tension in the ligament 10, the nuts 34, 34' may now be loosened by turning nuts 34, 34' in the opposite direction, thereby releasing the elements 30, 30' from engagement with the patient adjacent the bore hole 50. The releasable connection 48 may now be released by appropriately turning the insertion-tensioning device 29, 29' thereby turning the shaft 24 and releasing it from the element 44, 44' by undoing releasable couplings 48, 48'. The replacement ligament 10 is now in place under proper tension, by virtue of the engaging action of the elements 20, 20'.

Figure 5:
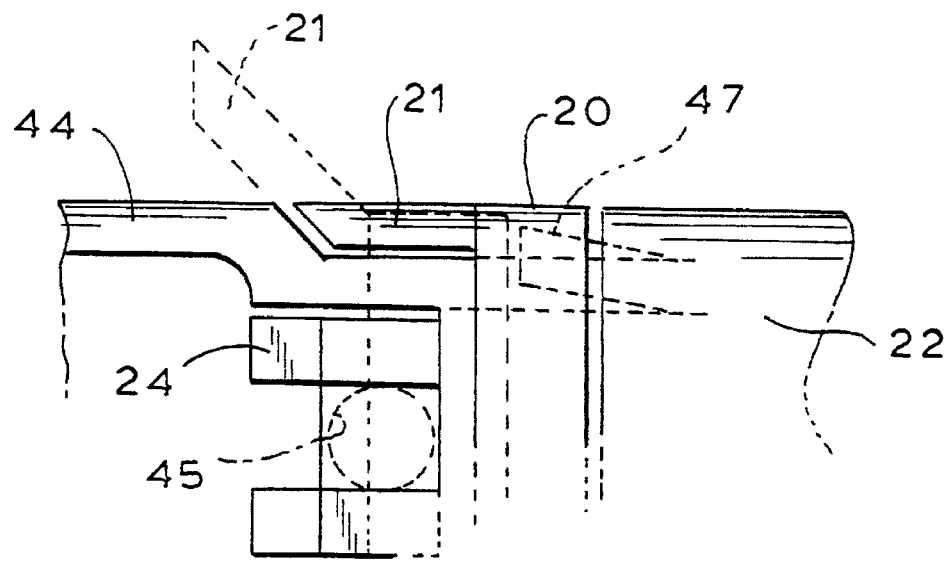
FIG. 5 shows, in a cross-section, details of the ligament securement device according to the present invention.

In order to insure that the engaging element 20 remains affixed to the ligament attaching element 44, the element 44 includes snap up projections 47 (see FIG. 2 and FIG. 5), which snap up out of the rear portion of the member 44 once the engaging element 20 has cleared the pop up projections 47. The pop up projections 47 may be made so that they spring up out of the member 44 and thereby prevent the engaging element 20 from moving back into the disengaged position. The inner diameter of the cylinder 22 may be made near the point where it engages with the engaging element 20 such that its walls do not interfere with the popping up action of the projections 47 when it slides over these projections. The above description applies equally to attachment 16 at the tibia end.

FIGS. 11A and 11b show an alternative to the snap-up projections 47. In the embodiment shown in these figures, the attaching element 44 includes a detent channel or groove 60 formed about a portion of its perimeter. A snap ring 62 is provided behind the fastener element 20. To engage the fingers 21 into the bore, the snap ring is pressed against the fastener element 20, forcing the fastener element against cam surface 42. Once the fingers 21 have extended, the snap ring 62 will snap into the detent channel 20, securely holding the fastener element 20 fingers 21 in the engaged position. Alternatively, snap ring 62 may be formed internally in fastener element 20 between element 20 and element 44, as shown in phantom in FIG. 11A at 62A.

FIG. 12 shows a further embodiment, adapted to allow varying degrees of finger 21 extension. In this embodiment, plural detent channels 60A, B, C and D are formed in element 44, shown in partial view. The channels have an abrupt leading edge 63 and inclined trailing edge 64. The abrupt leading edge allows the snap ring 62 to snap into the respective detent 60A, B, C or D without the chance of moving back. This prevents unintentional relaxation of the degree of finger 21 extension. The inclined trailing edge 64 allows the snap ring 62 to move forward to the next detent or groove to increase the degree of finger 21 extension, as desired.

Figure 8:
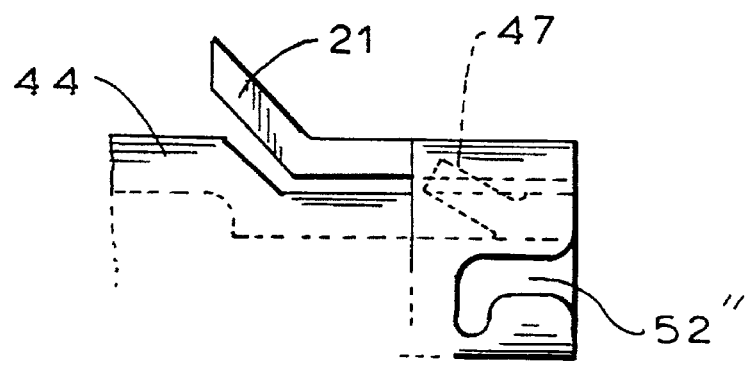
FIG. 8 shows a portion of an alternative embodiment of the securement device shown in FIG. 6.

As shown in FIG. 8, the releasable coupling 48 may have its mating elements reversed i.e., the pin 45, which is shown in FIGS. 5, 7A through 7C as being provided on the element 44, can instead be provided on the shaft 24, and the bayonet slots 52" may be provided on the element 44 instead.

Figure 6:
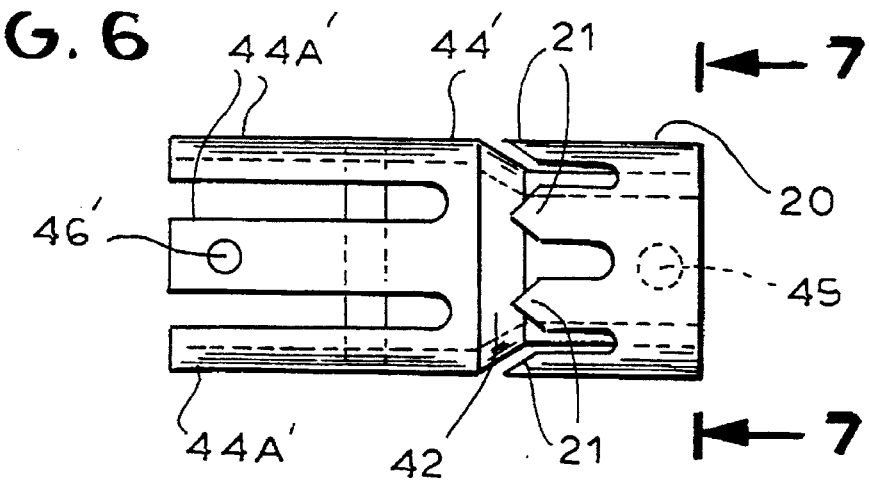
FIG. 6 shows a plan view of the alignment attachment device according to the present invention.

FIGS. 3 and 4 and 6 show an alternative embodiment for each end 16 and 18 of the device. In the embodiment shown in FIGS. 3 and 4, the ligament attaching element 44' has four prongs 44A' and two ligament attaching pins 46' and 46" connecting opposed ones of prongs 44A'. This provides additional attachment points for the secure attachment of the ligament to the attaching element 44A'.

In the alternative embodiment shown in FIG. 4, the ligament attaching pin comprises a separable pin 46A wherein one portion 46AA of a smaller diameter slips into the interior bore of the other pin portion 46BB. The prongs 44A in this embodiment can be spread apart to allow insertion of the replacement ligament 10, and in particular, allow the pin portions 46AA and 46BB to be spread so that they can be inserted through an opening in the replacement ligament 10.

All components of the present invention are made of suitable biocompatible materials, for example compatible metals such as stainless steel and/or biocompatible plastics.

Although the preferred embodiment described shows a replacement ligament 10, the invention is equally applicable to the reattachment of torn ligaments. Further, the preferred embodiment described shows a replacement ligament attached at both ends using the invention. It is equally, possible to secure such a replacement ligament, or a natural ligament, only at one end using the invention, and, as necessary, securing the other end using another technique or device.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. Apparatus for reattaching a ligament or implanting a ligament replacement in bone comprising:

a first ligament attaching element for coupling to a first end of the ligament or ligament replacement;

a second ligament attaching element for coupling to a second end of the ligament or ligament replacement;

a first engaging element slidably disposed on the first ligament attaching element and having at least one longitudinally extending finger;

a second engaging element slidably disposed on the second ligament attaching element and having at least one longitudinally extending finger;

the finger of each engaging element being directed toward each other, the first attaching element and first engaging element being adapted to be inserted in a first bore in a first bone member, the second attaching element and second engaging element being adapted to be inserted in a second bore in a second bone member aligned with the first bore, with the ligament or ligament replacement disposed between the attaching elements and in general alignment with the bores;

the first and second attaching elements each having cam surfaces thereon for engaging the at least one finger of the respective engaging element;

the finger of each engaging element being adapted to be moved into engagement with the cam surface thereby to force the finger to move outwardly into engagement with the wall of the bore in the respective bone member, thereby securing the engaging element into the respective bone member with the ligament or ligament replacement attached between the first and second attaching elements;

the first attaching element comprising a first securement point for the first end of the ligament or ligament replacement, the ligament or ligament replacement being secured in the first bore without being wedged between the attaching element and the wall of the first bore, the second attaching element comprising a second securement point for the second end of the ligament or ligament replacement, the ligament or ligament replacement being secured in the second bore without being wedged between the attaching element and the wall of the second bore.

2. The apparatus of claim 1, further wherein the first and second engaging elements have a plurality of circumferentially spaced longitudinally extending fingers for engagement into the respective bore.

3. The apparatus of claim 2, further comprising a holding member for holding a respective engaging element in position once the fingers have been extended into engagement with the respective bore.

4. The apparatus of claim 2 wherein the attaching elements comprise a plurality of prongs having at least one post therebetween for securement of the ligament replacement thereto.

5. The apparatus of claim 2, further comprising a fixing member for holding said attaching element in position in the respective bore.

6. The apparatus of claim 5, further comprising a force applying member for exerting a force on said engaging element while the fixing member holds the attaching element in a fixed position.

7. The apparatus of claim 6, further comprising a releasable coupling releasably attaching the fixing member to the attaching element.

8. The apparatus of claim 6 further comprising a tension applying member for exerting a tension in said attaching element and thereby to said ligament or ligament replacement.

9. The apparatus of claim 6, further comprising a fixing member for the other of said attaching elements and a force applying member for the other of said engaging elements.

10. The apparatus of claim 6, further comprising a replacement ligament for attachment at each end thereof to the attaching elements.

11. The apparatus of claim 7 wherein the releasable coupling comprises a bayonet coupling.

12. Apparatus for reattaching a ligament or implanting a ligament replacement in bone comprising:

a first ligament attaching element for coupling to a first end of the ligament or ligament replacement;

a second ligament attaching element for coupling to a second end of the ligament or ligament replacement;

a first engaging element slidably disposed on the first ligament attaching element and having at least one longitudinally extending finger;

a second engaging element slidably disposed on the second ligament attaching element and having at least one longitudinally extending finger;

the finger of each engaging element being directed toward each other, the first attaching element and first engaging element being adapted to be inserted in a first bore in a first bone member, the second attaching element and second engaging element being adapted to be inserted in a second bore in a second bone member aligned with the first bore, with the ligament or ligament replacement disposed between the attaching elements and in general alignment with the bores;

the first and second attaching elements each having cam surfaces thereon for engaging the at least one finger of the respective engaging element;

the finger of each engaging element being adapted to be moved into engagement with the cam surface thereby to force the finger to move outwardly into engagement with the wall of the bore in the respective bone member, thereby securing the engaging element into the respective bone member with the ligament or ligament replacement attached between the first and second attaching elements;

the first and second engaging elements having a plurality of circumferentially spaced longitudinally extending fingers for engagement into the respective bore; and further comprising a holding member for holding a respective engaging element in position once the fingers have been extended into engagement with the respective bore;

wherein the holding member comprises a snap-up projection on the attaching element which engages a circumferential portion of the engaging element to hold the fingers in an extended position.

13. Apparatus for reattaching a ligament or implanting a ligament replacement in bone comprising:

a first ligament attaching element for coupling to a first end of the ligament or ligament replacement;

a second ligament attaching element for coupling to a second end of the ligament or ligament replacement;

a first engaging element slidably disposed on the first ligament attaching element and having at least one longitudinally extending finger;

a second engaging element slidably disposed on the second ligament attaching element and having at least one longitudinally extending finger;

the finger of each engaging element being directed toward each other, the first attaching element and first engaging element being adapted to be inserted in a first bore in a first bone member, the second attaching element and second engaging element being adapted to be inserted in a second bore in a second bone member aligned with the first bore, with the ligament or ligament replacement disposed between the attaching elements and in general alignment with the bores;

the first and second attaching elements each having cam surfaces thereon for engaging the at least one finger of the respective engaging element;

the finger of each engaging element being adapted to be moved into engagement with the cam surface thereby to force the finger to move outwardly into engagement with the wall of the bore in the respective bone member, thereby securing the engaging element into the respective bone member with the ligament or ligament replacement attached between the first and second attaching elements;

the first and second engaging elements having a plurality of circumferentially spaced longitudinally extending fingers for engagement into the respective bore; and further comprising a holding member for holding a respective engaging element in position once the fingers have been extended into engagement with the respective bore;

wherein the holding member comprises a snap ring slidably disposed on the attaching element cooperating with the engaging element and a detent disposed in the attaching element into which the snap ring snaps thereby to hold the engaging element in position once the fingers have been extended.

14. The apparatus of claim 13, further comprising a plurality of detents in the attaching element into which the snap ring can snap, thereby to hold the fingers at varying degrees of extension.

15. The apparatus of claim 14, wherein the detents are formed with an abrupt leading edge so that the snap ring cannot move to relax the degree of finger extension and an inclined trailing edge so that the snap ring can be moved in a direction to increase the degree of finger extension.

16. Apparatus for reattaching a ligament or implanting a ligament replacement in bone comprising:

a first ligament attaching element for coupling to a first end of the ligament or ligament replacement;

a second ligament attaching element for coupling to a second end of the ligament or ligament replacement;

a first engaging element slidably disposed on the first ligament attaching element and having at least one longitudinally extending finger;

a second engaging element slidably disposed on the second ligament attaching element and having at least one longitudinally extending finger;

the finger of each engaging element being directed toward each other, the first attaching element and first engaging element being adapted to be inserted in a first bore in a first bone member, the second attaching element and second engaging element being adapted to be inserted in a second bore in a second bone member aligned with the first bore, with the ligament or ligament replacement disposed between the attaching elements and in general alignment with the bores;

the first and second attaching elements each having cam surfaces thereon for engaging the at least one finger of the respective engaging element;

the finger of each engaging element being adapted to be moved into engagement With the cam surface thereby to force the finger to move outwardly into engagement with the wall of the bore in the respective bone member, thereby securing the engaging element into the respective bone member with the ligament or ligament replacement attached between the first and second attaching elements;

the first and second engaging elements having a plurality of circumferentially spaced longitudinally extending fingers for engagement into the respective bore; and further comprising a fixing member for holding said attaching element in position in the respective bore;

a force applying member for exerting a force on said engaging element while the fixing member holds the attaching element in a fixed position;

wherein the fixing member comprises a shaft and the force applying member comprises a cylinder disposed concentrically about the shaft.

17. The apparatus of claim 16 wherein the cylinder has a surface portion adapted to receive a compression force, the cylinder being in engagement with a surface of the engaging element thereby to transmit the compressive force to the engaging element to cause the fingers of the engaging element to extend outwardly into engagement with the respective bore in the bone member.

18. Apparatus for reattaching a ligament or implanting a ligament replacement in bone comprising:

a first ligament attaching element for coupling to a first end of the ligament or ligament replacement;

a second ligament attaching element for coupling to a second end of the ligament or ligament replacement;

a first engaging element slidably disposed on the first ligament attaching element and having at least one longitudinally extending finger;

a second engaging element slidably disposed on the second ligament attaching element and having at least one longitudinally extending finger;

the finger of each engaging element being directed toward each other, the first attaching element and first engaging element being adapted to be inserted in a first bore in a first bone member, the second attaching element and second engaging element being adapted to be inserted in a second bore in a second bone member aligned with the first bore, with the ligament or ligament replacement disposed between the attaching elements and in general alignment with the bores;

the first and second attaching elements each having cam surfaces thereon for engaging the at least one finger of the respective engaging element;

the finger of each engaging element being adapted to be moved into engagement with the cam surface thereby to force the finger to move outwardly into engagement with the wall of the bore in the respective bone member, thereby securing the engaging element into the respective bone member with the ligament or ligament replacement attached between the first and second attaching elements;

the first and second engaging elements having a plurality of circumferentially spaced longitudinally extending fingers for engagement into the respective bore; and further comprising a fixing member for holding said attaching element in position in the respective bore;

a force applying member for exerting a force on said engaging element while the fixing member holds the attaching element in a fixed position;

a tension applying member for exerting a tension in said attaching element and thereby to said ligament or ligament replacement;

wherein the fixing member comprises a shaft and the force applying member comprises a cylinder disposed concentrically about the shaft.

19. The apparatus of claim 18, wherein the tension applying member comprises a contour member having a contoured surface adapted approximately to match the patient's body contour adjacent the respective bore in the bone member, the contour member having a threaded cylinder attached thereto which concentrically surrounds said cylinder, an adjusting nut disposed in threaded engagement with the threaded cylinder and being in engagement with an abutment fixed to the shaft, the nut being adjustable to apply a preset tension in the shaft and thereby to the ligament replacement.

20. The apparatus of claim 19 wherein the adjusting nut is adjustable to remove the tension in the shaft and to remove the contoured member from engagement with the patient, thereby to allow decoupling via a releasable coupling of said shaft from said engaging element.

21. Apparatus for reattaching a ligament or implanting a ligament replacement in bone comprising:

a first ligament attaching element for coupling to a first end of the ligament or ligament replacement;

a first engaging element slidably disposed on the first ligament attaching element and having at least one longitudinally extending finger;

the first attaching element and first engaging element being adapted to be inserted in a first bore in a first bone member, with the ligament or ligament replacement disposed between the attaching element and a second bone member;

the first attaching element having a cam surface thereon for engaging the at least one finger of the engaging element; and the finger of the engaging element being adapted to be moved into engagement with the cam surface thereby to force the finger to move outwardly into engagement with the wall of the bore in the first bone member, thereby securing the engaging element into the first bone member with the ligament or ligament replacement attached to the first attaching element;

the first attaching element comprising a first securement point for the first end of the ligament or ligament replacement, the ligament or ligament replacement being secured in the first bore without being wedged between the attaching element and the wall of the first bore.

* * * * *